United States Patent
Hsu et al.

(10) Patent No.: US 8,962,872 B2
(45) Date of Patent: Feb. 24, 2015

(54) METHOD FOR PREPARING EPOXIDES

(75) Inventors: Yu-Chuan Hsu, Taipei (TW); Cheng-Fa Hsieh, Taipei (TW); I-Hui Lin, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 13/614,684

(22) Filed: Sep. 13, 2012

(65) Prior Publication Data

US 2014/0046079 A1  Feb. 13, 2014

(30) Foreign Application Priority Data

Aug. 10, 2012 (TW) .............................. 101128916 A

(51) Int. Cl.
*C07D 301/03* (2006.01)
*C07D 301/06* (2006.01)

(52) U.S. Cl.
USPC .......................................... 549/523; 549/524

(58) Field of Classification Search
USPC .................................................. 549/523, 524
See application file for complete search history.

(56) References Cited

U.S. PATENT DOCUMENTS

| | | |
|---|---|---|
| 5,290,533 A | 3/1994 | Bellussi et al. |
| 5,888,471 A | 3/1999 | Bellussi et al. |
| 5,977,009 A | 11/1999 | Faraj |
| 6,042,807 A | 3/2000 | Faraj |
| 6,083,864 A | 7/2000 | Bellussi et al. |
| 6,252,095 B1 * | 6/2001 | Hayashi et al. ............... 549/523 |
| 6,329,537 B1 | 12/2001 | Faraj |
| 6,972,337 B1 | 12/2005 | Onimus et al. |
| 7,288,237 B2 | 10/2007 | Le-Khac |
| 8,362,183 B2 | 1/2013 | Vermeiren et al. |
| 8,518,370 B2 | 8/2013 | Vermeiren et al. |
| 2013/0041181 A1 * | 2/2013 | Chen et al. .................... 564/267 |

OTHER PUBLICATIONS

Sanchez et al. Applied Catalysis A: General 246 (2003) 69-77.*
Shetti et al. Journal of Molecular Catalysis A: Chemical 210 (2004) 171-178.*

* cited by examiner

*Primary Examiner* — Nizal Chandrakumar
(74) *Attorney, Agent, or Firm* — Mintz Levin Cohn Ferris Glovsky and Popeo, P.C.; Peter F. Corless; Richard B. Emmons

(57) ABSTRACT

A method for preparing an epoxide is disclosed. The method for preparing an epoxide includes the step of performing a reaction of an alkene and oxidant in the presence of a Ti—Si molecular sieve as a catalyst, and increases the conversion rate of hydrogen peroxide and the yield of the epoxide.

12 Claims, 1 Drawing Sheet

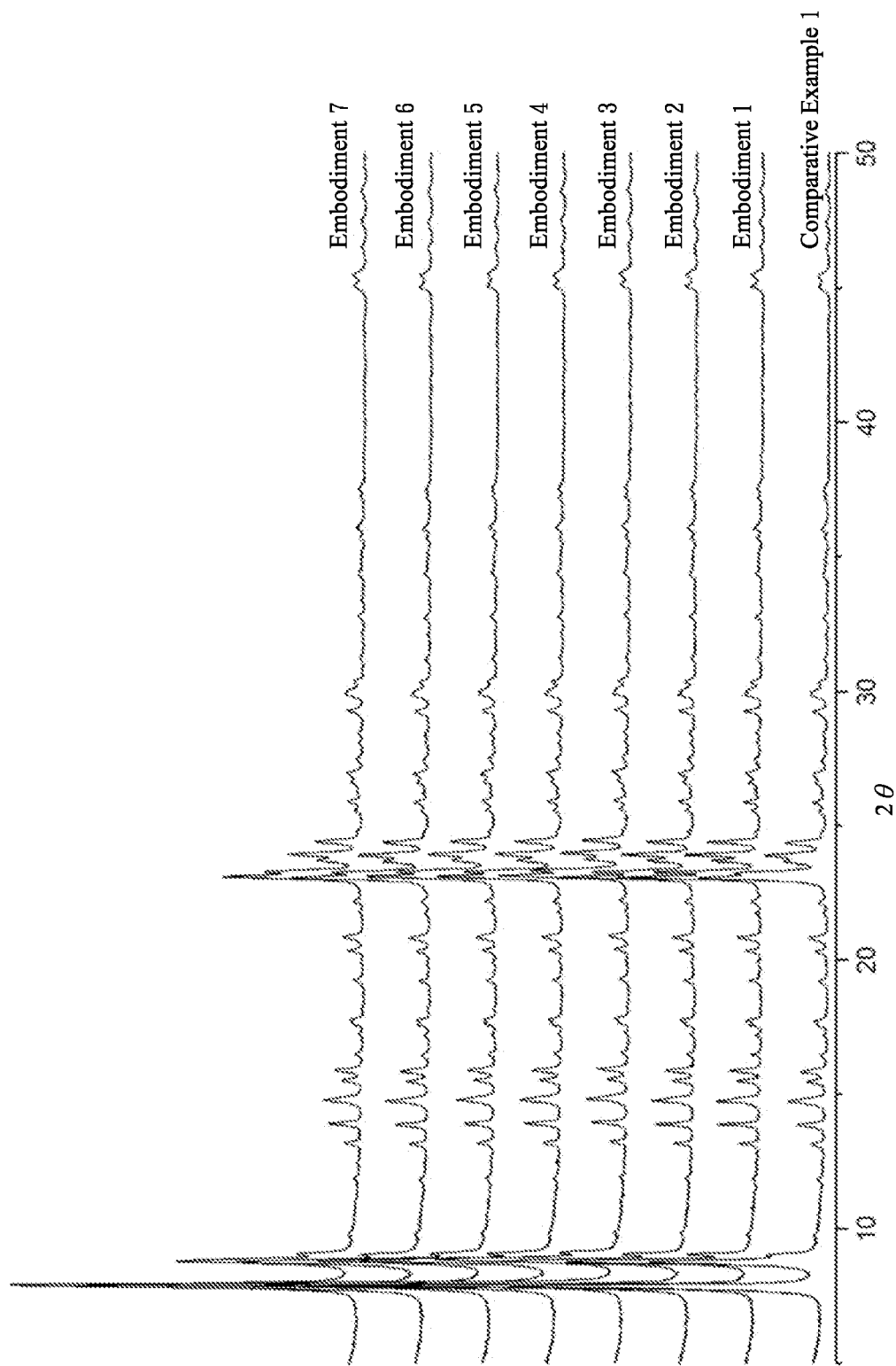

METHOD FOR PREPARING EPOXIDES

CROSS-REFERENCES TO RELATED APPLICATIONS

This application claims under 35 U.S.C. §119(a) the benefit of Taiwanese Application No. 101128916, filed Aug. 10, 2012, the entire contents of which is incorporated herein by reference.

BACKGROUND OF THE INVENTION

1. Field of the Invention

The present invention relates to methods for preparing an epoxide, and more particular to, a method for preparing an epoxide by using a Ti—Si molecular sieve as a catalyst.

2. Description of the Prior Art

There are various methods for preparing epoxides such as chlorohydrination, co-oxidation, direct oxidation and etc. In the chlorohydrination for preparing epoxides, chlorine-containing waste water is formed and causes pollution to environment. In the co-oxidation for preparing epoxides, the process is complicated and various joint products are formed. The direct oxidation may be oxygen direct oxidation or peroxide direct oxidation. In the oxygen direct oxidation, pure oxygen is the reactant, and the process is simple and has no intermediate, but the selectivity of the product is low. Currently, the peroxide direct oxidation is widely used, wherein a Ti—Si molecular sieve is used as a catalyst, and the catalyst is easily separated from the product. The peroxide direct oxidation causes no damage to environment, needs less oxygen, but has low selectivity and low yield of the epoxide.

Generally, crystal Ti—Si molecular sieves are prepared by a hydrothermal method. U.S. Pat. Nos. 5,290,533, 5,888,471, 5,977,009, 6,042,807, 6,083,864, 6,329,537, 6,972,337 and 7,288,237 disclose the hydrothermal methods. In the hydrothermal method for preparing a Ti—Si molecular sieve, the presence of an alkali metal ion or an alkaline earth metal ion causes unexpected formation of crystals, and thus catalytic activity of the Ti—Si molecular sieve is decreased, such that these metal ions should be avoided in the reaction solution.

Hence, there is a need to develop a method for preparing an epoxide with high conversion rate of reactants, high selectivity of products and high yield.

SUMMARY OF THE INVENTION

The present invention provides a method for preparing an epoxide. In the present invention, the method includes the step of performing a reaction of an alkene and oxidant in the presence of a Ti—Si molecular sieve of formula (I) as a catalyst $$(Mg_xTi_ySi)O_z \quad (I)$$

wherein x is in a range of from 0.001 to 0.05, y is in a range of from 0.005 to 0.1, and z is x+2y+2.

In an embodiment of the present invention, the Ti—Si molecular sieve has a structure of MFI, MEL, BEA, ZSM-48, MTW or MCM-41.

In accordance with the method of the present invention, the molar ratio of the alkene to the oxidant is in a range of from 1:100 to 100:1, and preferably in a range of from 1:10 to 10:1. The temperature of the reaction is not limited. Generally, the reaction is performed at a temperature in a range of from 0 to 150° C., and preferably at a temperature in a range of from 25 to 120° C. The reaction is performed for 1 minute to 48 hours, and preferably for 10 minutes to 8 hours. In accordance with the present invention, the method can be performed at any pressure, and preferably at 1 to 100 atm for increasing solubility of reactants. In the present invention, any reactor or equipment such as a fix bed, a transport bed, a fluid bed, a stir or a continue stir reactor can be used in a single or two phases system for the reaction.

In accordance with the present invention, there is no limitation to the amount of the catalyst. In an embodiment of the present invention, the method for preparing an epoxide is performed in batches. Generally, 1 mole of an alkene is used with 0.001 to 10 g of the Ti—Si molecular sieve. In another embodiment of the present invention, the method for preparing an epoxide is performed in a fix bed reactor. Generally, 1 to 100 moles of the alkene is used with the 1 kg/hr of the catalyst, and the concentration of Ti is maintained at 10 to 10000 ppm in the reaction system.

In the present invention, the method is simple, and has high conversion rate of hydrogen peroxide and high yield of the epoxide.

BRIEF DESCRIPTION OF THE DRAWINGS

FIG. 1 is a spectrum showing the PXRD of the Ti—Si molecular sieves according to the present invention.

DETAILED DESCRIPTION OF THE INVENTION

In the present invention, the Ti—Si molecular sieve has a formula (I):

$$(Mg_xTi_ySi)O_z \quad (I)$$

wherein x is in a range of from 0.001 to 0.05, y is in a range of from 0.005 to 0.1, and z is x+2y+2.

The T-Si molecular sieve can be a powder, a mass, a microball, a bulk or any other type.

In order to obtain the Ti—Si molecular sieve, the present invention further includes a method for preparing a Ti—Si molecular sieve. The method for preparing a Ti—Si molecular sieve includes mixing a Si source, a Ti source, an alkaline earth metal source and a template agent to form a mixture; heating the mixture to form a gel; heating the gel at 100 to 200° C. (preferably at 140 to 185° C.) for 1 hour to 10 days (preferably for 6 hours to 3 days); and then calcining the gel at 300 to 800° C. for 0.5 to 24 hours, so as to obtain the Ti—Si molecular sieve. In addition, the method for preparing the catalyst further includes provides a dispersion solution to the gel after the gel is formed, and heating the dispersion solution and the gel in a water bath, wherein the dispersion solution includes water and silicon dioxide sol.

The Ti—Si molecular sieve formed in the present invention can be isolated from the reaction solution by any proper conventional method such as filtration, centrifugation, decantation or any other method.

In accordance with the present invention, the Si source may be, but not limited to, silicon dioxide, silicon dioxide gel, silicon dioxide sol, a tetra-alkyl silicate such as tetramethyl silicate, tetraethyl silicate, tetramethyl silicate or tetrabutyl silicate. The silicon dioxide sol may be DuPont Ludox AS-40, Ludox AS-30, Ludox AM-30, Ludox TM-40, Ludox TM-50, Ludox HS-30, Ludox HS-40, Nissan Chemical SNOWTEX-40, SNOWTEX-50, SNOWTEX-C, SNOWTEX-N, SNOWTEX-20L, SNOWTEX-ZL, SNOWTEX-UP or other products.

In accordance with the present invention, the Ti source may be, but not limited to, a titanium salt (such as a titanium halide) or a tetra-alkyl titanate. In a preferred embodiment of the present invention, the Ti source may be, but not limited to, tetramethyl titanate, tetraethyl titanate, tetrapropyl titanate, tetra-n-butyl titanate, tetra-sec-butyl titanate, tetra-iso-butyl titanate, tetra-tert-butyl titanate, or a combination thereof.

In accordance with the present invention, the alkaline metal source is Mg source such as magnesium alkoxide or a magnesium salt such as a magnesium halide, magnesium hydroxide, magnesium carbonate, magnesium phosphate, magnesium sulfate, magnesium nitrate, magnesium acetate or magnesium silicate.

In accordance with the present invention, the template agent may be, but not limited to, nitrogen-containing organic material solution or alcohol solution, wherein the concentration of the nitrogen-containing organic material is 5 to 50 wt %, and is preferably 20 to 40 wt %. In a preferred embodiment of the present invention, the nitrogen-containing organic material may be, but not limited to, a alkylammonium hydroxide such as tetrapropylammonium hydroxide or tert-abutylammonium hydroxide; a alkylammonium halide such as aqueous solution or alcohol solution of tetrapropylammonium bromide or tetra-n-butylammonium bromide; and an organic amine such as triethylamine or diethylamine. The alcohol solution includes an alcohol having 1 to 5 carbon atoms such as methanol, ethanol, isopropanol, n-butanol or tert-butanol, and the solvent facilitates the crystallization of the Ti—Si molecular sieve.

In the method for preparing a T-Si molecular sieve of the present invention, a molar ratio of the nitrogen-containing organic alkaline material to silicon is in a range of from 0.1 to 0.5, preferably in a range of from 0.15 to 0.45, and more preferably in a range from 0.2 to 0.4.

The structure of the Ti—Si molecular sieve may be changed by altering the structure of the nitrogen-containing organic alkaline material. For example, the structure of the Ti—Si molecular sieve is MFI(ZSM-5), MEL(ZSM-11), BEA(beta), ZSM-48, MTW(ZSM-12), MCM-41 MFI(ZSM-5), MEL(ZSM-11), BEA(beta), ZSM-48, MTW(ZSM-12), MCM-41 MFI(ZSM-5), MEL(ZSM-11), BEA(beta), ZSM-48, MTW(ZSM-12), MCM-41 or any desired structure. For example, the Ti—Si molecular sieve can be the MFI configuration via tetrapropylammonium hydroxide.

In addition, other transition metals can be added in the Ti—Si molecular sieve of the present invention via immersion, precipitation, mixing or any other methods. For example, the transition metal solution is dispersed in a proper solvent via immersion, and mixed with the molecular sieve to form a Ti—Si molecular sieve with a transition metal, and then the molecular sieve is optionally dried and calcined. The amount of the transition metal is in a range of from 0.01 to 10 wt %, and preferably is in a range of from 0.05 to 5 wt %, based on the total weight of the Ti—Si molecular sieve of the present invention. The transition metal is disposed inside or outside of the configuration of the Ti—Si molecular sieve. While the Ti—Si molecular sieve with the transition metal is used in the reaction for preparing an epoxide, all or part of the transition metals is reduced.

In the method for preparing an epoxide of the present invention, an additional solvent can be used for dissolving reactants rather than the Ti—Si molecular sieve, providing a better control of the temperature and increasing the speed and selectivity of the epoxidation. The amount of the solvent is in a range of from 1 to 99% based on the total weight of reactants of the epoxidation, and the solvent is in a liquid phase at the temperature of the epoxidation.

In the method of the present invention, the solvent can be, but not limited to, ketone, ether, aliphatic compounds, aromatic carbohydrates, halogenated hydrocarbons, alcohol, water or excess amount of alkenes. The epoxidation is not adversely affected by water.

In the method of the present invention, an organic silylating agent, a water-soluble aqueous alkaline salt, a non-alkaline salt, a neutral salt, an acidic salt, a nitrogen-containing organic molecule, an organic acid or an inorganic acid with a nitrogen-containing salt, an ammonium carboxylate solution, a mixed solution of water and solvent, an acidic hydrogen peroxide solution, a fluorine ion precursor or a hydrogen peroxide solution with a fluorine ion can be used in the reaction for increasing selectivity of the reaction. U.S. Pat. Nos. 4,794,198, 4,824,976, 4,937,216, 5,646,314, 5,675,026, 6,060,610, 6,288,004, 6,300,506 and 7,148,381 are incorporated in the present invention.

In the present invention, the alkene may be, but not limited to, an organic compound having at least an ethylenyl group (C=C). The organic compound may be circular, branched or linear, and can include an aromatic group.

In an embodiment of the present invention, the alkene can be, but not limited to, a $C_{2-10}$alkenyl compound.

In an embodiment of the present invention, the alkene can be a monoalknyl compound, and the monoalkenyl compound is ethylene, propylene, 1-butylene, 2-butylene, 1-pentene or cyclohexene.

In an embodiment of the present invention, the oxidant is hydrogen peroxide, or any compound for producing or releasing hydrogen peroxide.

In the present invention, when the Ti—Si molecular sieve immersed with a transition metal is used as the catalyst, the hydrogen peroxide can be formed in situ. For example, hydrogen and oxygen are introduced into an epoxidation reactor containing the Ti—Si molecular sieve immersed with a transition metal (such as Pd or Pt) for producing hydrogen peroxide.

The following specific embodiments are provided to illustrate the disclosure of the present invention. These and other advantages and effects can be easily understood by those skilled in the art after reading the disclosure of this specification.

Comparative Example 1

A 500 ml flask was sealed under nitrogen, and added with 60 g of tetraethyl silicate and 112 g of tetrapropylammonium hydroxide in isopropanol (20 wt %). The mixture was stirred at 5V, and then added with 3.38 g of tetrabutyl titanate. Then, the mixture was stirred for 1 hour. The mixture was added slowly with 89.6 g of water, and then stirred for 1 hour, so as to obtain a gel mixture. Then, the alcohol was removed from the gel mixture at 85° C. for 1.5 hour. 21.60 g of silicon dioxide solution (40%) was dispersed in 147 g of water to form a dispersion solution. The dispersion solution was added in the gel mixture without alcohol, the mixture was stirred for 1 hour, and then the mixture was sealed in a stainless steel can with a Teflon lining. The mixture was heated at 180° C. for 120 hours. Then, the solid was separated from the liquid, and washed with water to be neutral. The solid was dried at 100° C., and calcined at 550° C. for 8 hours. Thus, the Ti—Si molecular sieve of Comparative Example 1 was obtained.

Preparation of the Ti—Si Molecular Sieve of the Present Invention

The Ti—Si molecular sieve has formula (I).

$$(Mg_xTi_ySi)O_z \qquad (I)$$

Embodiment 1

A 500 ml flask was sealed under nitrogen, and added with 60 g of tetraethyl silicate and 112 g of tetrapropylammonium hydroxide in isopropanol (20 wt %). The mixture was stirred at 5° C., and then added with 3.38 g of tetrabutyl titanate. Then, the mixture was stirred for 1 hour. 0.11 g of magnesium sulfate and 89.6 g of water were mixed, and then added into the flask. The mixture was stirred for 1 hour, so as to obtain a gel mixture. Then, the alcohol was removed from the gel mixture at 85° C. for 1.5 hour. 21.60 g of silicon dioxide solution (40%) was dispersed in 147 g of water to form a dispersion solution. The dispersion solution was added in the gel mixture without alcohol, the mixture was stirred for 1 hour, and then the mixture was sealed in a stainless steel can with a Teflon lining. The mixture was heated at 180° C. for 120 hours. Then, the solid was separated from the liquid, and washed with water to be neutral. The solid was dried at 100° C., and calcined at 550° C. for 8 hours. Thus, the Ti—Si molecular sieve of Embodiment 1 of the present invention was obtained. The PXRD spectrum of the Ti—Si molecular sieve of Embodiment 1 was shown in FIG. 1. As shown in FIG. 1, the Ti—Si molecular sieve of the present invention has the MFI structure, and has formula (I), wherein x is 0.001, y is 0.023 and z is 2.047.

Embodiments 2 to 7

The preparations of Embodiments 2 to 7 were similar to the preparation of Embodiment 1 except the amount of magnesium sulfate. The amounts of magnesium sulfate were respectively 0.53 g (Embodiment 2), 1.07 g (Embodiment 3), 2.13 g (Embodiment 4), 3.15 g (Embodiment 5), 4.26 g (Embodiment 6) and 5.32 g (Embodiment 7). The Ti—Si molecular sieves of Embodiments 2 to 7 of the present invention and the Ti—Si molecular sieves without additional metals (Comparative Example 1) all have the MFI structures, and have respective formula shown in Table 1.

TABLE 1

| | Embodiment 2 | Embodiment 3 | Embodiment 4 | Embodiment 5 | Embodiment 6 | Embodiment 7 |
|---|---|---|---|---|---|---|
| formula | $(Mg_{0.005}Ti_{0.023}Si)O_{2.051}$ | $(Mg_{0.01}Ti_{0.023}Si)O_{2.056}$ | $(Mg_{0.02}Ti_{0.023}Si)O_{2.066}$ | $(Mg_{0.03}Ti_{0.023}Si)O_{2.076}$ | $(Mg_{0.04}Ti_{0.023}Si)O_{2.086}$ | $(Mg_{0.05}Ti_{0.023}Si)O_{2.096}$ |

Preparation of an Epoxide

Embodiments 8 to 13

The Ti—Si molecular sieves of Comparative Example 1 and Embodiments 1 to 5 were respectively used as the catalyst for the preparation of epoxypropane from propylene and hydrogen peroxide.

In a 1 L high-pressure reactor, 3 g of the Ti—Si molecular sieve and 500 g of methanol were mixed, the pressure was formed with propylene to be 2 kg/cm², and the reaction temperature was maintained at 40° C. Then, 16.23 g of hydrogen peroxide (35 wt %) was introduced in the reactor at 1.0 ml/min, and the pressures was maintained with propylene to be 2 kg/cm². After the hydrogen peroxide was introduced into the reactor, the mixture was taken out, and the concentration of each product was analyzed by iodometric titration. The results were shown in Table 2.

TABLE 2

| | Catalyst | $X_{H2O2}$ (%) | $S_{PO}$ (%) | $Y_{PO}$ (%) |
|---|---|---|---|---|
| Embodiment 8 | Comparative Example 1 | 82.57 | 91.68 | 75.70 |

TABLE 2-continued

| | Catalyst | $X_{H2O2}$ (%) | $S_{PO}$ (%) | $Y_{PO}$ (%) |
|---|---|---|---|---|
| Embodiment 9 | Embodiment 1 | 90.94 | 91.01 | 82.77 |
| Embodiment 10 | Embodiment 2 | 91.99 | 91.60 | 84.26 |
| Embodiment 11 | Embodiment 3 | 92.06 | 91.71 | 84.43 |
| Embodiment 12 | Embodiment 4 | 91.70 | 92.51 | 84.83 |
| Embodiment 13 | Embodiment 5 | 84.02 | 96.71 | 78.10 |

$X_{H2O2}$ = conversion rate of hydrogen peroxide = consumption moles of hydrogen peroxide/total moles of introduced hydrogen peroxide × 100%
$S_{PO}$ = selectivity of epoxypropane = produced moles of epoxypropane/consumption moles of hydrogen peroxide × 100%;
$Y_{PO}$ = yield of epoxypropane = produced moles of epoxypropane/total moles of introduced hydrogen peroxide × 100%

Referring to Table 2, in comparison with Embodiment 8, the Ti—Si molecular sieve with the lower amount of magnesium ion (for example, Embodiment 9 or 10) increases the conversion rate of hydrogen peroxide and significantly increases the yield of epoypropane at the same selectivity of epoxypropane. In addition, in comparison with Embodiment 8, the Ti—Si molecular sieves of Embodiments 11 to 13 having the increased amount of magnesium ion increase the selectivity of epoxypropane. Accordingly, the method of the present invention is simple, and has high conversion rate of hydrogen peroxide and high yield of epoxides.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing an epoxide, comprising the step of: performing a reaction of an alkene and an oxidant in the presence of a Ti—Si molecular sieve of formula (I) as a catalyst $$(Mg_xTi_ySi)O_z \qquad (I)$$

wherein x is in a range of from 0.001 to 0.05, y is in a range of from 0.005 to 0.1, and z is x+2y+2; wherein the catalyst is prepared by preparing a mixture of tetrabutyl titanate, tetraethyl silicate, tetrapropylammonium hydroxide in isopropanol, magnesium sulfate, and water; heating the mixture to form a gel mixture; mixing a colloidal silica with the gel mixture; heating the gel mixture mixed with the colloidal silica in a water bath; and calcining the gel mixture mixed with the colloidal silica.

2. The method of claim 1, wherein the Ti—Si molecular sieve has a structure of MFI, MEL, BEA, ZSM-48, MTW or MCM-41.

3. The method of claim 1, wherein a molar ratio of the alkene to the oxidant is in a range of from 1:100 to 100:1.

4. The method of claim 1, wherein the alkene is a $C_{2-10}$ alkenyl compound.

5. The method of claim 4, wherein the alkene is a-monoalkenyl compound.

6. The method of claim 5, wherein the monoalkenyl compound is ethylene, propylene, 1-butylene, 2-butylene, 1-pentene or cyclohexene.

7. The method of claim 5, wherein a molar ratio of the monoalkenyl compound to the oxidant is in a range of from 1:10 to 10:1.

8. The method of claim 1, wherein the oxidant is hydrogen peroxide.

9. The method of claim 1, wherein a solvent is further provided, and the solvent is water, an alcohol having 1 to 5 carbon atoms or a combination thereof.

10. The method of claim 1, wherein methanol is provided as a solvent.

11. The method of claim 1, wherein the reaction is performed at a temperature of from 0 to 150° C.

12. The method of claim 11, wherein the reaction is performed at a temperature of from 25 to 120° C.

* * * * *